United States Patent [19] [11] 4,115,440
Sheng et al. [45] Sep. 19, 1978

[54] SELENIUM CATALYZED DECOMPOSITION OF PEROXIDE INTERMEDIATES RESULTING FROM THE AUTOXIDATION OF ACROLEIN AND METHACROLEIN

[75] Inventors: Ming Nan Sheng; Jar-lin Kao, both of Cherry Hill, N.J.

[73] Assignee: Atlantic Richfield Company, Los Angeles, Calif.

[21] Appl. No.: 788,722

[22] Filed: Apr. 19, 1977

[51] Int. Cl.[2] ...................... C07C 51/32; C07C 57/04
[52] U.S. Cl. .................................... 562/533; 562/598
[58] Field of Search ...................... 260/530 N, 526 N

[56] References Cited

U.S. PATENT DOCUMENTS 2,212,900 8/1940 Groll et al. .................... 260/530 N

FOREIGN PATENT DOCUMENTS 373,326 5/1932 United Kingdom ................ 260/530 N
694,417 7/1953 United Kingdom ................ 260/530 N

*Primary Examiner*—Vivian Garner
*Attorney, Agent, or Firm*—Delbert E. McCaslin

[57] ABSTRACT

A process for the preparation of acrylic acid or methacrylic acid which comprises catalytically decomposing or converting in the presence of selenium the peroxide (peroxy) compounds formed during autoxidation or contained in the oxidate solution derived from the autoxidation of the respective acrolein or methacrolein, particularly, the conversion of permethacrylic acid and methacrolein monopermethacrylate to methacrylic acid.

17 Claims, No Drawings

SELENIUM CATALYZED DECOMPOSITION OF PEROXIDE INTERMEDIATES RESULTING FROM THE AUTOXIDATION OF ACROLEIN AND METHACROLEIN

BACKGROUND OF THE INVENTION

When $\alpha,\beta$-unsaturated aliphatic aldehydes such as acrolein or methacrolein are oxidized in the liquid phase with oxygen or an oxygen-containing gas such as air, peroxide (peroxy) compounds are co-produced along with the corresponding $\alpha,\beta$-unsaturated carboxylic acids. A mixture of products are obtained in the resulting oxidate solution formed by the oxidation. Based on the total weight, the oxidate solution will generally contain unreacted aldehyde of from 20 to 70 weight percent, and from 40 to 10 weight percent of the corresponding acrylic or methacrylic acid product as well as peroxide (peroxy) compounds of the unsaturated aldehyde feed materials and peroxide (peroxy) compounds of the unsaturated acid product and other by-products. The unsaturated peroxide (peroxy) compounds co-produced during the autoxidation of acrolein and methacrolein to acrylic acid and methacrylic acid would be peracrylic acid and acrolein monoperacrylate and permethacrylic acid and methacrolein monopermethacrylate respectively.

The present invention relates to a process for the selenium catalyzed conversion or decomposition of the above described unsaturated peroxide compounds co-produced by the autoxidation of the unsaturated aldehydes (acrolein or methacrolein). The selenium catalyzed decomposition may be carried out during the autoxidation of the aldehyde or after the autoxidation stage is completed. Employment of the selenium catalyst during the oxidation step of the aldehyde provides an in situ conversion of the intermediate peroxide compounds to the desired acid product. The oxidate product solution of the autoxidation of an aldehyde containing the mixture of products as hereinabove described may be treated according to the process of this invention; the process to catalytically decompose the peroxides being carried out after the aldehyde has been oxidized and the intermediate peroxide compounds formed. Conversion of the peroxide compounds according to this invention provides for a high selectivity to the acid and for the recovery of large percentages of the desired unsaturated carboxylic acid (acrylic or methacrylic) as well as a minimum amount of polymer formation, resulting in high overall yield of the acid from the particular original unsaturated aldehyde as compared to prior art processes, including straight thermal decomposition of peroxide compounds. Post catalytic decomposition of the oxidate, i.e., after completion of the oxidation of the aldehyde is preferred to in situ decomposition in that peroxide conversions are substantially complete and a higher selectivity to methacrylic or acrylic acid is obtained.

Various catalytic vapor phase processes have been described employing complex catalyst systems. Liquid phase reactions include the use of hydroperoxides, molecular oxygen including air in the presence of various solvents and various organic and inorganic metal compounds of silver, nickel, cobalt, manganese, copper, chromium and vanadium used singly, in combination and with other materials such as bromine compounds and chelates. Generally the oxidation of unsaturated aliphatic aldehydes to the corresponding acid in the liquid phase has been difficult due to polymerization of the unsaturated acids when formed and the co-production of various undesirable peroxides of the unsaturated acids and aldehydes formed during oxidation, resulting in low selectivity to and yield of the unsaturated acids.

U.S. Pat. No. 3,114,769 in an attempt to prevent polymeric by-products, describes a liquid phase process for the oxidation of methacrolein or acrolein to the corresponding acid and peroxide compounds in the presence of molecular oxygen and a small quantity of iodine. The products of the oxidation contained mixtures of unsaturated acids, and large amounts of both acid and aldehyde peroxides and unreacted aldehydes. After separation the peroxide products were separately decomposed to the acid by subjecting the oxidate containing peroxides to the catalytic effect of a protonic acid such as p-toluene sulfonic acid and an alcohol forming a hot solvent solution as is further described in U.S. Pat. No. 3,253,025.

In an article by William F. Brill and Fred Lister, Journal of Organic Chemistry, Vol. 26, pp. 565–569, 1961 the metal-salt catalyzed oxidation of methacrolein in acetic acid is described. The methacrolein goes to peroxide products, acid and major amounts of soluble polymer.

An article by Benjamin Phillips, et al, Journal of the American Chemical Society, Vol. 76, pp. 5982–5986, 1957 shows the preparation of peracetic acid by the autoxidation of acetaldehyde and with peracetic acid and acetaldehyde monoperacetate as intermediates. At temperatures above 20° C. the acetaldehyde monoperacetate decomposes readily yielding acetic acid. Straight thermal decomposition of the $\alpha,\beta$-unsaturated aliphatic aldehyde peroxy intermediates, such as methacrolein monopermethacrylate and acrolein monoperacrylate does not selectively give high yield of the respective acrylic and methacrylic acids and in addition the rate of reaction is low.

To date no commercially successful process has been developed for the preparation of acrylic acid or methacrylic acid involving the autoxidation of the corresponding $\alpha,\beta$-unsaturated aldehyde and the conversion of the co-produced peroxide intermediate.

The acrylic and methacrylic acid products obtained by the process of this invention have many known commercial uses, particularly for the preparation of esters such as methyl methacrylate and as monomers for polymer formation.

A particular advantage of the process of the present invention is the discovery that catalytic amounts of selenium per se, organic and inorganic selenium compounds or mixtures thereof permit the respective peroxide (peroxy) compounds formed during oxidation of the unsaturated aldehyde to be selectively decomposed or converted to the acid, e.g., methacrolein monopermethacrylate to methacrylic acid providing an overall process advantage in the liquid phase autoxidation of the aldehyde to produce the desired unsaturated acid.

SUMMARY OF THE INVENTION

According to the present invention there is provided a much improved process for the decomposition of unsaturated peroxide (peroxy) intermediate compounds resulting from the autoxidation of the unsaturated aldehydes, acrolein and methacrolein, by converting the respective co-produced peroxides during the autoxidation stage or in the oxidate after the autoxidation step to its corresponding unsaturated carboxylic acid, acrylic or methacrylic, at a suitable temperature in the presence of a catalytic amount of a selenium catalyst or mixtures thereof.

It is a primary object of this invention to provide a process for the liquid phase preparation of acrylic acid from acrolein or methacrylic acid from methacrolein in high yield by converting or decomposing resulting by-product peroxide compounds to the acid and to avoid operational problems associated with prior processes.

It is another object of this invention to provide a novel reaction system useful in the conversion or decomposition of co-produced peroxide intermediate compounds to the desired acid produced by the autoxidation.

It is a further object of this invention to provide a specific mechanism for the employment of selenium catalysts for the conversion of peroxide compounds to acids.

These and other objects and advantages of this invention will become apparent from the description of the invention which follows and from the claims.

DESCRIPTION OF THE INVENTION

According to the invention a process has been discovered in which high yield $\alpha,\beta$-unsaturated aliphatic carboxylic acids, i.e., acrylic or methacrylic acid, may be obtained from the autoxidation of the corresponding $\alpha,\beta$-unsaturated aliphatic aldehyde, i.e., acrolein or methacrolein wherein intermediate unsaturated peroxides are co-produced. Principally, the invention comprises a process of catalytically decomposing the unsaturated peroxide compounds during or after autoxidation of the aldehyde at a suitable temperature in the presence of selenium and/or selenium compounds thereof to obtain increased yield of the acid and avoid the formation of undesired amounts of polymer. After the autoxidation of the unsaturated aldehyde the co-produced peroxide compounds are catalytically decomposed in the oxidate and this oxidate as are the oxidates resulting from in situ decomposition are further processed to recover total product acid.

The oxidate including the intermediate peroxide compounds which may be treated according to this invention may be prepared by the oxidation, in the liquid phase, of acrolein or methacrolein to produce acrylic or methacrylic acid. Any method for the preparation of the acids which co-produces the peroxide intermediates may be employed which results in a liquid phase containing any unreacted aldehyde (acrolein or methacrolein), acid product (acrylic or methacrylic acid), peroxides of the aldehyde and the acid (acrolein monoperacrylate and peracrylic acid, and methacrolein monopermethacrylate and permethacrylic acid) together with other by-products such as acetic acid. The unreacted aldehyde (acrolein or methacrolein) may if desired, be distilled from the oxidate prior to or during the catalytic decomposition of the peroxides.

The oxidation process, to produce the acid and peroxide compounds, may be carried out in the liquid phase on the feed acrolein or methacrolein with or without an inert solvent or catalyst in a suitable reactor at temperatures of from about 0° C. to 100° C. and pressures from about atmospheric to 1500 psig by contacting the aldehyde with oxygen or an oxygen-containing gas, such as described, for example, in U.S. Pat. Nos. 3,114,769, 3,155,719 and 3,253,025. The oxidate produced by such processes may be treated by the process of the present invention to convert the intermediate peroxides to the desired acid or the intermediate peroxides produced during such processes decomposed in situ to the desired acid.

In any liquid phase oxidation process generally about 30 percent of the feed acrolein or methacrolein will be converted to the desired unsaturated product acid and the corresponding peroxides co-produced during oxidation and in the resulting oxidate will generally amount to from about 5 to 30 weight percent of the total weight of the oxidate.

While lower amounts of polymer formation result from the process of this invention, it is generally desirable, but not essential, to add a polymerization inhibitor to the oxidate solution when subjecting the oxidate to post catalytic decomposition by the process of this invention. Suitable inhibitors include compounds containing an aromatic nucleus such as hydroquinone, pyrogallol, p-methoxyphenol, cresol, resorcinol and phenol, e.g., 2,6-di-tert-butyl-4-methylphenol. The amount of inhibitor added may be between about 0.01 and 1.0 weight percent of the oxidate.

The selenium catalysts which may be utilized in the process of this invention are selenium itself or an organic or inorganic selenium compound or mixtures thereof. Any organic or inorganic selenium salt having an anion which does not unduly retard the formation of the desired acid products by an extraneous side reaction can be utilized as a catalyst to decompose the peroxide intermediates.

Representative selenium catalyts, in addition to selenium per se include, for example, inorganic selenium compounds such as selenium dioxide, trioxide, sulfide, disulfide, chloride, oxychloride and bromide, selenious acid and selenic acid. Metallic selenium compounds such as aluminum selenide, zinc selenide and selenite, sodium selenide, selenite and selenate, bismuth selenide, and antimony selenide may be employed as well as organic selenium compounds such as diethylselenite, diethyldiselenide, dioctylselenide, dioctyldiselenide, diphenylselenide or diselenide and phenylseleninic acid. The preferred catalysts are selenium dioxide, selenious acid, selenium trioxide, diphenyl diselenide and diphenyl selenide.

The selenium catalysts may be present in solution or suspension and may also be on support materials which will not affect the decomposition of the peroxide compounds or react with the other products of the oxidate such as alumina, silica gel, aluminosilicates, activated carbon or zeolites. The catalysts may be partially or completely soluble under process conditions and are preferably in a finely divided state.

The decomposition reaction is carried out in the presence of a catalytic proportion of the selenium catalyst and will proceed with small amounts of the representative compounds or selenium per se as hereinabove described. Generally the amount of catalyst employed after completion of the autoxidation of the aldehyde (post decomposition) in accordance with the present invention will be equivalent to between about 0.001 and 10 percent by weight and preferably between about 0.01 and 1.0 percent by weight of the oxidate reaction mixture containing the peroxide compounds to be decomposed. The proportions of the selenium catalysts used during the autoxidation of the aldehyde (in situ decomposition) will be equivalent to between about 0.0001 to 0.1 mole and preferably in amounts of between about 0.001 to 0.01 mole of catalyst per mole of the unsaturated aldehyde being oxidized.

While not essential inert organic solvents may be employed in the in situ decomposition or post decomposition process of this invention. The autoxidation reaction of the unsaturated aldehyde (acrolein or methacrolein) to prepare the corresponding unsaturated carboxylic acids in which the selenium catalyzed in situ decomposition of the co-produced peroxides by the process of this invention may be carried out is generally conducted in the liquid phase in which the aldehyde is dissolved in an inert solvent or mixture of solvents. The concentration of unsaturated aldehyde in the mixture of solvents and aldehyde may be between about 5 percent and 90 percent and preferably between about 20 percent and 80 percent by weight of the aldehyde-solvent solution.

Post selenium catalyzed decomposition of the peroxides contained in the oxidate solution derived from the liquid phase autoxidation of acrolein or methacrolein may also be carried out in the presence of an organic solvent. The oxidate solution containing the peroxides may already contain a solvent which was employed during oxidation. If necessary additional solvent or mixtures of solvents may be employed.

The solvents employed in the process of the invention must be inert under the peroxide decomposition reaction conditions used, i.e., non-reactive under the process conditions used, and preferably should be easily separable from the reaction mixture and components thereof including the unreacted aldehyde starting material, any intermediate products and acid product.

The solvents which may be employed in concentrations of from about 10 to 95 weight percent, preferably 20 to 80 weight percent of the solvent-aldehyde mixture or solvent-oxidate mixture and suitable for use in the process of the present invention can be aliphatic, cycloaliphatic and aromatic hydrocarbons and halogenated hydrocarbons including halogenated aromatic hydrocarbons, carboxylic acids, ethers, esters and amides. Certain inert tertiary alcohols such as tertiary octyl alcohol, and small amounts of primary and secondary alcohols in admixture with the other solvents, e.g., up to about 40 percent by weight of the solvent mixture, may also be employed. Representative solvents especially suitable for use in this invention include benzene, toluene, o-, m-, and p-xylenes, hexane, cyclohexane, ethylcyclohexane, pentane, chlorobenzene, bromobenzene, chlorotoluene, carbon tetrachloride, chloroform, methylene chloride, acetic acid, ethyl acetate, butyl acetate, methyl acetate, cyclohexyl acetate, methyl benzoate, tetrahydrofuran, dioxane, dimethylformamide, N,N'-dimethyl acetamide, 1,2-dichlorotetrafluroroethane, etc. While solvents or mixtures of solvents are preferably employed in the process of this invention, during autoxidation and in situ decomposition, some of the aldehydes which may be employed may be oxidized in the presence of catalytic amounts of the selenium catalyst without the use of a solvent particularly if the selenium catalyst is essentially soluble in the liquid aldehyde.

The oxygen-containing gas employed in carrying out the oxidation process and the in situ peroxide decomposition by the instant invention is generally oxygen itself or air. Air is included by the phrase "oxygen-containing gas" as are relatively pure oxygen gas and other oxygen-containing gases. Oxygen itself may be diluted with an inert gas such as nitrogen, carbon dioxide or helium.

The oxidation and in situ decomposition reaction is conducted at moderate temperatures, generally between 0° C. and 100° C. or 20°–80° C. and preferably at temperatures of from about 65° C. and 75° C. and under sufficient pressure to maintain a liquid reaction phase. The reaction may be carried out at higher or lower temperatures with superatmospheric or subatmospheric pressures. The reaction may be carried out at atmospheric pressure and pressures of up to about 1500 psig may be employed. Elevated pressures of from about 50 psig to about 500 psig are particularly advantageous. When using an unsaturated aldehyde and/or solvent which may be relatively volatile, elevated pressures may be necessary to ensure reaction in the liquid phase.

The process for the post catalytic decomposition of the peroxides contained in the oxidate solution may be carried out at temperatures of from about ambient (about 25° C.) to 100° C. and preferably at temperatures of from about 30° C. to 60° C. The process may be conducted at atmospheric, sub-atmospheric or superatmospheric pressures. However, atmospheric pressure is preferred and provides the best result.

The process of the invention may be carried out batchwise, semi-continuous or continuous in any suitable reactor. A general procedure for carrying out the post decomposition process of the invention is to add the catalyst to the oxidate reaction product containing the peroxide (peroxy) compounds and heat the mixture to the desired temperature for the appropriate period. The catalyst is added to the autoxidation reactants for in situ decomposition of the peroxides as formed during oxidation of the aldehyde. The reaction products, after decomposition of peroxides by in situ or post decomposition, may be recovered and treated by any conventional method such as, for example, by distillation, by extracting the acid with a base and subsequent acidification, or by solvent extraction.

The reaction time to catalytically decompose the peroxide compounds to the respective unsaturated acid may vary between a few minutes and several hours and is generally dependent on the peroxide being decomposed, temperature of reaction and whether the process is continuous or batch.

The following examples are provided to illustrate the invention in accordance with the principles of this invention but are not to be construed as limiting the invention in any way except as indicated by the appended claims. Unless otherwise noted, percentages are in terms of percent by weight.

In the Examples which follow, the in situ decomposition of peroxides was carried out during the autoxidation of acrolein or methacrolein in the presence of selenium. The feed material for the catalytic post decomposition of the peroxide (peroxy) compounds to the acid was obtained by the autoxidation of acrolein or methacrolein in the absence of added catalyst. The unsaturated aldehyde (acrolein or methacrolein) was charged to a suitable reactor (polytetrafluoroethylene-lined reactors, stainless steel autoclave or aluminum autoclave) along with a solvent and with or without a selenium catalyst. The mixture was stirred and heated at 45° C. under a pressure of 200 psig oxygen. Oxygen was added whenever there was a 5 psig pressure drop. After 40 psig of oxygen was reacted, the mixture was cooled and the pressure slowly vented. The reaction product (oxidate) and a wash solvent was recovered from the autoclave and 0.1 g. of 2,6-di-tert-butyl-4-methylphenol as a polymerization inhibitor added. For post decomposition of the peroxides the oxidate was subjected to a catalytic decomposition by the process of this invention.

Analysis of the oxidate solution and the decomposition reaction product solutions were conducted as follows: Samples were titrated by differential potassium iodide to determine permethacrylic acid and methacrolein monopermethacrylate or peracrylic acid and acrolein monoperacrylate. Samples were also reduced with triphenylphosphine and analyzed by gas-liquid chromatography to determine any methacrolein or acrolein content, as well as methacrylic or acrylic acid and acetic acid content.

In the Examples the following abbreviations are used:

MA - methacrolein
MAA - methacrylic acid
PMAA - permethacrylic acid
EtOH - ethyl alcohol
MMPM - methacrolein monopermethacrylate
TBA - tertiary butyl alcohol
HOAc - acetic acid
$Et_2SeO_3$ - diethyl selenite
$(C_6H_5)_2Se$ - diphenyl selenide

EXAMPLE 1

An oxidate containing a mixture of unreacted methacrolein, permethacrylic acid, methacrolein monopermethacrylate, solvent, acetic acid, methacrylic acid product and minor amounts of other by-products were prepared by charging methacrolein and solvent to a 700 ml. aluminum autoclave equipped with a stirrer. The mixture was stirred and heated to 45° C. under 200 psig air. After 5 psig of pressure drop, oxygen was added to the autoclave until 40 psig oxygen was reacted. The reactor was cooled and vented and the reaction product oxidate washed with 46 g. of the same solvent (providing 98 g. total solvent) employed in an autoxidation. 0.5 g. of 2,6-di-tert-butyl-4-methylphenol was added to inhibit any polymerization. Runs employing 3.0 g. portions of the reaction product oxidates were heated in the presence of various selenium catalysts with stirring on a constant temperature bath to catalytically decompose the peroxide compounds. 3.0 g. portions of oxidate were also heated in the absence of catalyst for comparison. The results are summarized in Table I which clearly shows the advantages and effect of selenium catalyzed decomposition over straight thermal treatment.

EXAMPLE 2

The procedure of Example 1 for autoxidation was repeated using acrolein to form an oxidate containing a mixture of unreacted acrolein, peracrylic acid, acrolein monoperacrylate, n-hexane solvent (98 g. total after wash) and minor amounts of other by-products including acetic acid. A 3.0 g. portion of the oxidate containing 10.8 millimoles peracrylic acid and 36.2 millimoles of acrolein monoperacrylate was heated with stirring to 55° C. on a constant temperature bath for 3 hours in the presence of 0.60 weight percent concentration of selenium dioxide. Analysis of the oxidate after the decomposition reaction showed a 90 percent peroxide decomposition with a 90 percent selectivity to acrylic acid.

EXAMPLE 3

A 90.0 g. portion of the oxidate as used in Run 1, Example 1 containing n-hexane solvent to which 0.9 weight percent of selenium dioxide was added was heated with stirring to 80° C. on a constant temperature bath for a period of 3 hours to decompose the peroxides while contained methacrolein and n-hexane were being distilled off at 60°-68° C. Most of the methacrolein and n-hexane was removed from the oxidate solution. The residue analyzed by iodometry showed no peroxide compounds present indicating a 100 percent conversion. The methacrylic acid was recovered by distillation under reduced pressure (1 to 15 torr) at 40° C. bath temperature. Analysis showed a 75 percent selectivity to methacrylic acid.

EXAMPLE 4

A number of oxidate solutions resulting from the autoxidation of methacrolein were prepared by the procedure of Example 1 employing various solvents and mixtures of solvents and 0.5 g. of 2,6-di-tert-butyl-4-methylphenol added to inhibit any polymerization. Runs employing 90.0 g. portions of the reaction product oxidates, unless otherwise noted, were distilled at 0° C. under 15 torr pressure to remove between 60 and 85 percent of the unreacted methacrolein and solvent from the oxidate avoiding explosive tendencies of the peroxides PMAA and MMPM and any non-selective thermal decomposition thereof. Selenium catalyst was added to the oxidate residue containing the remaining methacrolein and solvent and the mixture heated to 55° C. on a constant temperature bath for 4 hours to catalytically decompose the peroxide compounds and the reaction products analyzed. A run was also carried out in the absence of catalyst for comparision. The results are summarized in Table II.

TABLE 1

Post Catalytic Decomposition of Peroxide Compounds (PMAA & MMPM)

| Run No. | Solvent | Catalyst | Concentration Wt. % | Temp. ° C. | Time hr. | Peroxides in Oxidate (millimoles) MMPM | PMAA | % Peroxide % Decomposition | Selectivity to MAA[2] |
|---|---|---|---|---|---|---|---|---|---|
| 1 | n-hexane | $SeO_2$ | 0.5 | 30 | 17 | 36.0 | 14.0 | 78 | 91 |
| 2 | n-hexane | $SeO_2$ | 5.0 | 30 | 41 | 36.0 | 14.0 | 81 | 92 |
| 3 | n-hexane | $SeO_2$ | 5.0 | 55 | 4 | 36.0 | 14.0 | 84 | 84 |
| 4 | n-hexane | $SeO_2$ | 0.5 | 65 | 2 | 36.0 | 14.0 | 80 | 71 |
| 5 | n-dodecane | Se | 0.4 | 60 | 4 | 35.9 | 12.8 | 80 | 80 |
| 6 | $CCl_4$ | $SeBr_4$ | 4.0 | 50 | 4 | 37.1 | 14.0 | 68 | 90 |
| 7 | Cyclohexane | $SeO_3$ | 0.3 | 60 | 4 | 38.0 | 12.9 | 86 | 87 |
| 8 | Benzene | $Se_2Cl_2$ | 0.5 | 50 | 2 | 37.3 | 13.8 | 72 | 90 |
| 9 | Benzene | $Et_2SeO_3$ | 0.7 | 50 | 4 | 37.3 | 13.8 | 67 | 88 |
| 10[1] | n-hexane | none | 0 | 50 | 2 | 36.0 | 14.0 | 1 | —(negligible) |
| 11[1] | n-hexane | none | 0 | 60 | 3 | 36.0 | 14.0 | 58 | 48 |

[1]Comparative runs - no catalyst added.
[2]Selectivity was calculated on the basis of the stoichiometry that MMPM yielded two moles of methacrylic acid during decomposition.

TABLE 2

Post Catalytic Peroxide Conversion-Distillation of Unreacted Methacrolein

| Run No. | Solvent (g.) | Catalyst | Concentration Wt. %[1] | Peroxides in Oxidate (millimoles) MMPM | PMAA | % Peroxide Decomposition | % MA Conversion[3] | % MAA Selectivity |
|---|---|---|---|---|---|---|---|---|
| 1 | n-hexane (7.0) | $SeO_2$ | 0.25 | 36.0 | 14.0 | 99 | 14 | 94 |
| 2 | n-hexane (7.0) | $SeO_2$ | 0.25 | 36.0 | 14.0 | 100 | 15 | 82 |
| 3 | n-hexane (7.0) | $SeO_2$ | 0.30 | 36.0 | 14.0 | 100 | 19 | 86 |
| 4[2] | n-hexane (7.0) | $SeO_2$ | 0.40 | 36.0 | 14.0 | 100 | 22 | 86 |
| 5 | n-hexane/TBA (7.0/1.0) | $SeO_2$ | 1.0 | 37.2 | 14.1 | 100 | 26 | 76 |
| 6 | n-hexane/EtOH (8.0/2.0) | $Et_2SeO_3$ | 0.33 | 36.8 | 13.7 | 100 | 26 | 73 |
| 7 | Cyclohexane/$CCl_4$ (8.0/2.0) | $SeCl_4$ | 0.40 | 37.9 | 12.1 | 100 | 20 | 80 |
| 8 | n-hexane/Dioxane (7.0/1.0) | $(C_6H_5)_2Se$ | 0.50 | 35.8 | 13.4 | 100 | 25 | 73 |
| 9 | Benzene/HOAc (8.0/1.0) | $H_2SeO_3$ | 0.35 | 37.3 | 13.8 | 100 | 23 | 79 |
| 10[4] | n-hexane (7.0) | none | — | 36.0 | 14.0 | 48 | 20 | 38 |

[1] The concentration was calculated on the basis of the original oxidate.
[2] Selenium catalyst added to oxidate prior to distillation and peroxide decomposition.
[3] % Methacrolein Conversion based on original autoxidation after decomposition step.
[4] Comparative run - no catalyst added.

EXAMPLE 5

A 90.0 g. portion of the oxidate solution of Example 2 containing a mixture of unreacted acrolein 10.8 millimoles peracrylic acid, 36.2 millimoles acrolein monoperacrylate, 55 g. of n-hexane and minor amounts of other by-products such as acetic acid was distilled at 0° C. under 15 torr pressure to remove about 75 percent of the unreacted acrolein and solvent. A concentration of 0.39 weight percent selenium dioxide based on the original oxidate was added to the distillation residue solution and the mixture heated to 55° C. for ½ hour to catalytically decompose peracrylic acid and acrolein monoperacrylate. Analysis of the reaction products showed a 100 percent peroxide decomposition with an 82 percent selectivity to acrylic acid. Total conversion of the original acrolein to acrylic acid (autoxidation and decomposition steps) was 22 percent.

EXAMPLE 6

A number of runs were carried out employing a selenium catalyst for in situ decomposition of intermediate peroxide compounds during the autoxidation of methacrolein to methacrylic acid. A cylindrical aluminum reactor having a 45 ml. capacity was treated with a hot (80° C.) 30 percent solution of hydrogen peroxide, rinsed with acetone and dried in air. 2.0 g. of methacrolein, 4.50 g. of the solvent used and the selenium catalyst was charged to the reactor. The mixture was agitated by a magnetic stirrer at 70° C. reaction temperature under 100 psig of oxygen pressure. After reacting 40 psig of oxygen, the mixture was cooled in a dry ice-isopropanol bath and the pressure slowly vented. To prevent any polymerization of the reaction products during recovery, 0.1 g. of 2,6-di-tert-butyl-4-methylphenol was added.

The catalyst, solvents, reaction conditions and analytical results are summarized in Table 3. Run numbers 1 and 2 of Table 3 are comparative with no catalyst employed.

TABLE 3

Autoxidation of Methacrolein-In situ Decomposition of Peroxides

| Run No. | Solvent (g.) | Catalyst | Conc.[4] Wt. % | Temp. °C. | Time (Min.) | % MA[1] Conv. | % Selectivity to[5] MMPM | PMAA | MAA | Other By-Products |
|---|---|---|---|---|---|---|---|---|---|---|
| 1[2] | n-hexane (4.50) | none | 0 | 70 | 78 | 33 | 46 | 8 | 20 | 26 |
| 2[2] | n-hexane/EtOH[3] (3.2/1.3) | none | 0 | 70 | 115 | 35 | 47 | 6 | 22 | 25 |
| 3 | n-hexane/EtOH[3] (3.2/1.3) | $SeO_2$ | 0.16 | 70 | 142 | 29 | 19 | 3 | 44 | 34 |
| 4 | $CCl_4$ (4.0) | $SeCl_4$ | 0.25 | 70 | 100 | 30 | 18 | 2 | 46 | 34 |
| 5 | Cyclohexane/EtOH[3] (3.2/1.3) | $H_2SeO_3$ | 0.20 | 70 | 110 | 31 | 19 | 3 | 45 | 33 |
| 6 | Benzene (4.5) | $(C_6H_5)_2Se$ | 0.30 | 70 | 115 | 32 | 19 | 4 | 43 | 34 |

[1] % Methacrolein conversion, total including autoxidation and peroxide decomposition.
[2] Comparative run - no catalyst added.
[3] A blended solvent of 60 wt. % of paraffin and 10 wt. % of alcohol.
[4] The concentration was calculated on the basis of the total charge.
[5] Total % selectivity to products including autoxidation and peroxide decomposition.

EXAMPLE 7

The procedure for Example 6 was repeated using acrolein instead of methacrolein. The reactor was charged with 3.0 g. of acrolein 4.50 g. of n-hexane solvent and 0.26 weight percent selenium dioxide. The mixture was agitated by a magnetic stirrer at 55° C. temperature for 215 minutes. After reacting 40 psig oxygen, the mixture was cooled in a dry ice-isopropanol bath and the reactor vented. 0.1 g. of 2,6-di-tert-butyl-4-methylphenol was added to prevent any polymerization. Analysis of the reaction products showed a 30 percent conversion of acrolein with a selectivity to acrylic acid of 49 percent, peracrylic acid 2 percent, acrolein monoperacrylate 15 percent and other by-products including acetic acid of 34 percent.

EXAMPLE 8

The procedure of Example 1 for autoxidation was repeated using n-pentane as the solvent to form an oxidate containing a mixture of unreacted methacrolein (15.8 weight percent), permethacrylic acid (0.83 weight percent ), methacrolein monopermethacrylate (2.3 weight percent), methacrylic acid (3.3 weight percent), n-pentane (77.6 weight percent), and minor amounts of other byproducts including acetic acid (< 0.2 weight percent). To 80.3 g. portions of the oxidate, there was added 0.53 g. of selenium dioxide and 0.05 g. of 2,6-di-tert-butyl-4-methylphenol. The mixture was distilled at 0° C. bath temperature under 15 torr of pressure to give 64.9 g of distillate (containing 6.5 g. of methacrolein and 58.4 g. of n-pentane) and 15.6 g. of residue. The residue was heated at 35° C. for 20 hours. Analysis showed that 94 mole percent of the peroxide was decomposed catalytically by selenium dioxide and that the over-all process gave 95 percent selectivity to methacrylic acid at 19 percent methacrolein conversion.

We claim:

1. A process for the preparation of acrylic acid or methacrylic acid which comprises catalytically decomposing at a temperature in the range of from about 0° C. to about 100° C. in the presence of a selenium catalyst selected from the group consisting of elemental selenium, selenium dioxide, trioxide, sulfide, disulfide, chloride, oxychloride and bromide, selenious acid, selenic acid, aluminum selenide, sodium selenide, sodium selenite, sodium selenate, diethylselenite, diethyldiselenide, dioctylselenide, dioctyldiselenide, diphenylselenide, diphenyldiselenide and phenylseleninic acid, or mixtures thereof, the corresponding peracrylic acid and acrolein monoperacrylate or permethacrylic acid and methacrolein monopermethacrylate intermediate peroxide compounds formed during the liquid phase autoxidation of acrolein or methacrolein, or contained in an oxidate solution derived from and after said liquid phase autoxidation, and recovering the acrylic or methacrylic acid.

2. A process according to claim 1 wherein the peroxide compounds are decomposed in situ during the liquid phase autoxidation of acrolein or methacrolein at a temperature in the range of about 0° C. to about 100° C. in the presence of from about 0.0001 to about 0.1 mole of a selenium catalyst per mole of acrolein or methacrolein being oxidized.

3. A process according to claim 2 wherein the process is carried out at a temperature between about 65° C. and 75° C. in the presence of from about 0.001 to 0.01 mole of a selenium catalyst per mole of acrolein or methacrolein being oxidized.

4. A process according to claim 2 wherein an inert organic solvent is employed at concentrations of from about 10 to 95 weight percent of the solvent-aldehyde mixture and is selected from the group consisting of aliphatic, cycloaliphatic or aromatic hydrocarbons, halogenated hydrocarbon, carboxylic acids, ethers, esters, amides and alcohols or mixtures thereof.

5. A process according to claim 4 wherein the solvent is selected from n-hexane, carbon tetrachloride, benzene or mixtures of cyclohexane and ethyl alcohol, pentane, and n-hexane and ethyl alcohol.

6. A process according to claim 1 wherein the peroxide compounds are contained in an oxidate reaction mixture derived from the liquid phase autoxidation of acrolein or methacrolein, said peroxide compounds in said oxidate solution being decomposed at a temperature of from about ambient to about 100° C. in the presence of from about 0.001 to about 10 percent by weight of the oxidate reaction solution of a selenium catalyst.

7. A process according to claim 6 wherein the process is carried out at a temperature between about 30° and 60° C. in the presence of from about 0.01 to about 1.0 percent by weight of a selenium catalyst based on the oxidate reaction solution.

8. A process according to claim 6 wherein an inert organic solvent is employed in the oxidate solution at concentrations of from about 10 to about 95 weight percent of the solvent-oxidate mixture and is selected from the group consisting of aliphatic, cycloaliphatic or aromatic hydrocarbons, halogenated hydrocarbon, carboxylic acids, ethers, esters, amides and alcohols or mixtures thereof.

9. A process according to claim 8 wherein the solvent is selected form n-hexane, n-dodecane, carbon tetrachloride, cyclohexane, benzene, dioxane or mixtures of n-hexane and t-butyl alcohol, n-hexane and ethyl alcohol, cyclohexane and carbon tetrachloride, n-hexane and dioxane and benzene and acetic acid.

10. A process according to claim 1 wherein the selenium catalyst is selected from selenium per se, selenium dioxide, selenium bromide, selenium trioxide, selenium chloride, diethyl selenite, diphenyl selenide and selenious acid or mixtures thereof.

11. A process according to claim 1 wherein the selenium catalyst is supported.

12. A process for the preparation of acrylic acid which comprises the steps of:

oxidizing acrolein with oxygen or an oxygen-containing gas in the liquid phase to produce a reaction product oxidate containing unreacted acrolein, peracrylic acid, acrolein monoperacrylate, acrylic acid and other by-products;

adding from about 20 to 80 weight percent of an aliphatic, cycloaliphatic or aromatic hydrocarbon, halogenated hydrocarbon, carboxylic acid, ether, ester, alcohol or amide solvent or mixture thereof to said oxidate to form a solvent-oxidate mixture;

subjecting the solvent-oxidate mixture to a temperature in the range of from about 30° to 60° C. in the presence of from about 0.01 to 1.0 percent by weight of a selenium catalyst selected from the group consisting of elemental selenium, selenium dioxide, trioxide, sulfide, disulfide, chloride, oxychloride and bromide, selenious acid, selenic acid, aluminum selenide, sodium selenide, sodium selenite, sodium selenate, diethylselenite, diethyldiselenide, dioctylselenide, dioctyldiselenide, diphenylselenide, diphenyldiselenide and phenylseleninic acid, or mixtures thereof to catalytically decompose peracrylic acid and acrolein monoperacrylate to acrylic acid; and recovering said acrylic acid produced by said oxidation and catalytic decomposition.

13. A process according to claim 12 wherein the unreacted acrolein or solvent in the reaction product oxidate is removed by distillation prior to or during the decomposition step.

14. A process for the preparation of methacrylic acid which comprises the steps of:

oxidizing methacrolein with oxygen or an oxygen-containing gas in the liquid phase to produce a reaction product oxidate containing unreacted methacrolein, permethacrylic acid, methacrolein monopermethacrylate, methacrylic acid and other by-products;

adding from about 20 to 80 weight percent of an aliphatic, cycloaliphatic or aromatic hydrocarbon, halogenated hydrocarbon, carboxylic acid, ether, ester, alcohol or amide solvent or mixture thereof to said oxidate to form a solvent-oxidate mixture;

subjecting the solvent-oxidate mixture to a temperature in the range of from about 30° to 60° C. in the presence of from about 0.01 to 1.0 percent by weight of a selenium catalyst selected from the group consisting of elemental selenium, selenium dioxide, trioxide, sulfide, disulfide, chloride, oxychloride and bromide, selenious acid, selenic acid, aluminum selenide, sodium selenide, sodium selenite, sodium selenate, diethylselenite, diethyldiselenide, dioctylselenide, dioctyldiselenide, diphenylselenide, diphenyldiselenide and phenylseleninic acid, or mixtures thereof to catalytically decompose permethacrylic acid and methacrolein monopermethacrylate to methacrylic acid; and recovering said methacrylic acid produced by said oxidation and catalytic decomposition.

15. A process according to claim 14 wherein the unreacted methacrolein or solvent in the reaction product oxidate is removed and recovered by distillation prior to or during the decomposition step.

16. A process for the preparation of acrylic acid which comprises contacting an inert solvent solution of acrolein with oxygen or an oxygen-containing gas at a temperature of from about 20° to 80° C. and a pressure of between about 50 psig and 500 psig in the presence of from about 0.001 to 0.01 mole of a selenium catalyst selected from the group consisting of elemental selenium, selenium dioxide, trioxide, sulfide, disulfide, chloride, oxychloride, and bromide, selenious acid, selenic acid, aluminum selenide, sodium selenide, sodium selenite, sodium selenate, deithylselenite, diethyldiselenide, dioctylselenide, dioctyldiselenide, diphenylselenide, diphenyldiselenide and phenylseleninic acid, or mixtures thereof per mole of acrolein to effect a catalytic in situ decomposition of intermediate peracrylic acid and acrolein monoperacrylate formed during oxidation of the acrolein to acrylic acid.

17. A process for the preparation of methacrylic acid which comprises contacting an inert solvent solution of methacrolein with oxygen or an oxygen-containing gas at a temperature of from about 20° to 80° C. and a pressure of between about 50 psig and 500 psig in the presence of from about 0.001 to 0.01 mole of a selenium catalyst selected from the group consisting of elemental selenium, selenium dioxide, trioxide, sulfide, disulfide, chloride, oxychloride and bromide, selenious acid, selenic acid, aluminum selenide, sodium selenide, sodium selenite, sodium selenate, diethylselenite, diethyldiselenide, dioctylselenide, dioctyldiselenide, diphenylselenide, diphenyldiselenide and phenylseleninic acid, or mixtures thereof per mole of methacrolein to effect a catalytic in situ decomposition of intermediate permethacrylic acid and methacrolein monopermethacrylate formed during oxidation of the methacrolein to methacrylic acid.

* * * * *